(12) United States Patent
Laufer et al.

(10) Patent No.: US 10,239,827 B2
(45) Date of Patent: Mar. 26, 2019

(54) BIS[3-ISOPROPENYL-α,α-DIMETHYLBENZYL]CARBODIIMIDE, PRODUCTION METHODS, AND USE OF SAID COMPOUND

(71) Applicant: RHEIN CHEMIE RHEINAU GMBH, Mannheim (DE)

(72) Inventors: Wilhelm Laufer, Ellerstadt (DE); Martina Schoenhaber, Darmstadt (DE); Armin Eckert, Oberhausen-Rheinhausen (DE); Oliver Herd, Wuppertal (DE); Rolf Sperber, Wuppertal (DE)

(73) Assignee: LANXESS Deutschland GmbH, Cologne (DE)

( * ) Notice: Subject to any disclaimer, the term of this patent is extended or adjusted under 35 U.S.C. 154(b) by 30 days.

(21) Appl. No.: 15/315,498

(22) PCT Filed: Jun. 3, 2015

(86) PCT No.: PCT/EP2015/062410
§ 371 (c)(1),
(2) Date: Dec. 1, 2016

(87) PCT Pub. No.: WO2015/185645
PCT Pub. Date: Dec. 10, 2015

(65) Prior Publication Data
US 2017/0088509 A1    Mar. 30, 2017

(30) Foreign Application Priority Data
Jun. 4, 2014  (EP) .................................... 14171202

(51) Int. Cl.
*C07C 267/00* (2006.01)
*C08G 18/81* (2006.01)
*C08G 18/02* (2006.01)
*C08K 5/29* (2006.01)
*C08L 75/06* (2006.01)
*C08G 18/09* (2006.01)

(52) U.S. Cl.
CPC ............ *C07C 267/00* (2013.01); *C08G 18/02* (2013.01); *C08G 18/025* (2013.01); *C08G 18/095* (2013.01); *C08G 18/81* (2013.01); *C08K 5/29* (2013.01); *C08L 75/06* (2013.01)

(58) Field of Classification Search
CPC ................................ C07C 267/00; C08K 5/29
See application file for complete search history.

(56) References Cited

U.S. PATENT DOCUMENTS 5,352,400 A    10/1994    West

FOREIGN PATENT DOCUMENTS

WO    WO 2005/111136    *   11/2005

OTHER PUBLICATIONS

WO 2005-111136 machine translation. Original document date (2005).*
Neumann, W. et al. "The Preparation of Carbodiimides from Isocyanates", Angew. Chem. Internat. Edit., vol. 1, Verlag Chemie GmbH (1962), No. 12, pp. 621-625.
Wagner, Kuno et al., "a, w-Diisocyanatocarbodiimides, -Polycarbodiimides, and Their Derivatives", Angew. Chem. Int. Ed., Engl. 20, Verlag Chemie GmbH, 1981, pp. 819-830.
International Search Report from International Application No. PCT?EP2015/062410, dated Jul. 21, 2015, two pages.

* cited by examiner

*Primary Examiner* — Edward J Cain

(57) ABSTRACT

The present invention relates to novel processes for producing bis[3-isopropenyl-α,α-dimethylbenzyl]carbodiimide, to the thus-produced bis[3-isopropenyl-α,α-dimethylbenzyl]carbodiimide and to the use thereof as a hydrolysis inhibitor in polyurethane (PU)-based systems, preferably thermoplastic TPU, PU adhesives, PU casting resins, PU elastomers or PU foams.

10 Claims, No Drawings

BIS[3-ISOPROPENYL-α,α-DIMETHYLBENZYL]CARBODIIMIDE, PRODUCTION METHODS, AND USE OF SAID COMPOUND

The invention relates to novel processes for producing bis[3-isopropenyl-α,α-dimethylbenzyl]carbodiimide, to the thus-produced bis[3-isopropenyl-α,α-dimethylbenzyl]carbodiimide and to the use thereof as a hydrolysis inhibitor in polyurethane (PU)-based systems, preferably thermoplastic TPU. PU adhesives, PU casting resins, PU elastomers or PU foams.

Carbodiimides have proven useful in many applications, for example as hydrolysis inhibitors for thermoplastics, polyols, polyurethanes, triglycerides and lubricating oils etc.

In the prior art the synthesis of carbodiimides proceeds from isocyanates which are carbodiimidized under basic or heterocyclic catalysis to eliminate $CO_2$. This allows mono- or polyfunctional isocyanates to be converted into monomeric or polymeric carbodiimides.

The typically used catalysts are alkali metal or alkaline earth metal compounds and also heterocyclic compounds comprising phosphorus, see Angew. Chem. 1962, 74, 801-806 and Angew. Chem. 1981, 93, 855-866.

The production of bis[3-isopropenyl-α,α-dimethylbenzyl]carbodiimide is difficult since the end product can often be obtained only in low yield, see WO-A 2005/111136 where the synthesis of bis[3-isopropenyl-α,α-dimethylbenzyl]carbodiimide from 3-isopropenyl-α,α-dimethylbenzylisocyanate with the heterocyclic phosphorus compound 1-methyl-2-phospholene-1-oxide (MPO) as catalyst is described and a yield of only 37% is achieved.

Also difficult is the complete removal of the generally used phosphorus-containing catalyst. Since carbodiimides are preferably employed in the production of polyurethanes, the presence of phosphorus, even in trace amounts, is extremely disruptive and is therefore to be avoided.

The prior art syntheses are accordingly not economic and bis[3-isopropenyl-α,α-dimethylbenzyl]carbodiimide therefore cannot be commercially supplied and employed for hydrolysis inhibition of polyesters and ester-based PU systems.

The present invention accordingly has for its object to provide an improved process allowing production of bis[3-isopropenyl-α,α-dimethylbenzyl]carbodiimide in high yield and additionally resulting in a bis[3-isopropenyl-α,α-dimethylbenzyl]carbodiimide that is free from organic phosphorus compounds and may therefore be employed in the production and/or stabilization of PU systems.

It has now been found that, surprisingly, these abovementioned objects are achieved when bis[3-isopropenyl-α,α-dimethylbenzyl]carbodiimide is converted (carbodiimidized) by conversion of 3-isopropenyl-α,α-dimethylbenzylisocyanate in the presence of 0.1-20 wt % of basic cesium salts as catalyst at temperatures between 160° C. to 220° C. to eliminate carbon dioxide.

The invention accordingly provides a process for producing bis[3-isopropenyl-α,α-dimethylbenzyl]carbodiimide whereby 3-isopropenyl-α,α-dimethylbenzylisocyanate is carbodiimidized in the presence of 0.1-20 wt %, preferably 0.5-10 wt %, particularly preferably 1-5 wt % of basic cesium salts at temperatures between 160° C. to 220° C., preferably 180° C. to 210° C., particularly preferably 190° C. to 200° C.

In the context of the invention the basic cesium salts employed are preferably cesium carbonate and/or cesium alkoxide, preferably cesium methoxide and/or cesium ethoxide.

In a preferred embodiment of the process according to the invention the basic cesium salts are filtered off following the carbodiimidization.

In a further preferred embodiment of the process according to the invention the carbodiimidization takes place in a solvent.

Preferred solvents are mono-, di-, tri- or polyalkyl-substituted, preferably dialkyl-substituted benzenes and/or dibenzenes, where alkyl=$C_1$-$C_3$. Particularly preferred alkylbenzenes are xylenes.

The present invention further provides the bis[3-isopropenyl-α,α-dimethylbenzyl]carbodiimide obtainable by the process according to the invention which preferably has a proportion of heterocyclic phosphorus compounds, in particular 1-methyl-2-phospholene-1-oxide (MPO), of less than 1 ppm and which is particularly preferably free from heterocyclic phosphorus compounds.

The present invention accordingly also provides a stabilizer comprising at least 90 wt % of bis[3-isopropenyl-α,α-dimethylbenzyl]carbodiimide produced by the process according to the invention and comprising not more than 1 ppm of heterocyclic phosphorus compounds.

Bis[3-isopropenyl-α,α-dimethylbenzyl]carbodiimide conforms to the following formula:

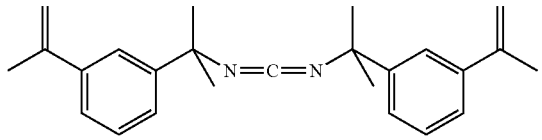 [SMILES: C=C(C)c1cccc(C(C)(C)N=C=NC(C)(C)c2cccc(C(=C)C)c2)c1]

In addition, the present invention further provides a process for producing polyurethanes (PU), preferably thermoplastic polyurethanes, whereby the reaction of the polyols, preferably of the polyester polyols, with the diisocyanates is performed in the presence of the bis[3-isopropenyl-α,α-dimethylbenzyl]carbodiimide according to the invention optionally in the presence of catalysts and optionally further assistant and additive substances.

Production of the polyurethanes is preferably effected in the manner described in WO 2005/111136 A1 using the bis[3-isopropenyl-α,α-dimethylbenzyl]carbodiimide according to the invention as stabilizer. Polyaddition reaction of polyisocyanates with polyhydric alcohols, the polyols, forms polyurethanes virtually quantitatively. The linkage arises through the reaction of an isocyanate group (—N═C═O) of one molecule with a hydroxyl group (—OH) of another molecule to form a urethane group (—NH—CO—O—).

Thermoplastic polyurethanes are polyurethanes that are formable under application of heat.

The progress of the reaction between diisocyanate and polyol is dependent on the molar ratio of the components. Intermediates having desirable average molecular weight and desirable end groups may readily be obtained. These intermediates may then be reacted (chain-extended) with a diol or diamine at a later juncture to then form the desired polyurethane or polyurethane-polyurea hybrid. The intermediates are generally referred to as prepolymers.

The molar ratio of diisocyanate and polyol is preferably between 1:2 to 10:1. Suitable polyols for the production of prepolymers are polyalkylene glycol ethers, polyether esters or polyesters having terminal hydroxyl groups (polyester polyols).

The polyols in the context of the invention are compounds preferably having a molecular weight in (g/mol) of up to 2000, preferably in the range from 500 to 2000 and particularly preferably in the range from 500 to 1000.

The term "polyol" in the context of the invention encompasses both diols and triols, and also compounds having more than three hydroxyl groups per molecule. The use of triols is particularly preferred.

Preferred polyols are polyester polyols and/or polyether ester polyols.

It is advantageous when the polyol has an OH number of up to 200, preferably between 20 and 150 and particularly preferably between 50 and 115.

Especially suitable are polyester polyols being reaction products of various polyols with aromatic or aliphatic dicarboxylic acids and/or polymers of lactones.

Preference is given here to aromatic dicarboxylic acids which may be used for forming suitable polyester polyols. Particular preference is given here to terephthalic acid, isophthalic acid, phthalic acid, phthalic anhydride and substituted dicarboxylic acid compounds having a benzene ring.

Preferred aliphatic dicarboxylic acids are those that may be used for forming suitable polyester polyols, particularly preferably sebacic acid, adipic acid and glutaric acid.

Preferred polymers of lactones are those that may be used for forming suitable polyester polyols, particularly preferably polycaprolactone.

Both the dicarboxylic acids and the polymers of lactones are commodity chemicals.

Particular preference is also given to polyols that may be used for forming suitable polyester polyols, very particularly preferably ethylene glycol, butanediol, neopentyl glycol, hexanediol, propylene glycol, dipropylene glycol, diethylene glycol and cyclohexanedimethanol.

In a further preferred embodiment of the invention, the polyols are polyether ester polyols.

Preferred therefor are the reaction products of various aforementioned polyols with aromatic or aliphatic dicarboxylic acids and/or polymers of lactones, preferably polycaprolactone.

The polyols employed in the context of the inventions are commodity chemicals obtainable from Bayer MaterialScience AG under the trade names Baycoll® and Desmophen®.

Preferred diisocyanates are aromatic and aliphatic diisocyanates. Particular preference is given to toluene 2,4-diisocyanate, toluene 2,6-diisocyanate, phenylene diisocyanate, 4,4-diphenylmethane diisocyanate, methylenebis(4-phenyl isocyanate), naphthalene 1,5-diisocyanate, tetramethylene 1,4-diisocyanate and/or hexamethylene 1,6-diisocyanate, very particular preference to toluene 2,4-diisocyanate and toluene 2,6-diisocyanate.

The diisocyanates employed in the context of the inventions are commodity chemicals obtainable from Bayer MaterialScience AG under the trade name Desmodur®.

In a further embodiment of the invention, the composition additionally comprises at least one diamine and/or diol.

Preferred diamines employed for the chain extension are 2-methylpropyl 3,5-diamino-4-chlorobenzoate, bis(4,4'-amino-3-chlorophenyl)methane, 3,5-dimethylthio-2,4-tolylenediamine, 3,5-dimethylthio-2,4-tolylenediamine, 3,5-diethyl-2,4-tolylenediamine, 3,5-diethyl-2,6-tolylenediamine, 4,4'-methylenebis(3-chloro-2,6-diethylaniline) and 1,3-propanediol bis(4-aminobenzoate).

Preferred diols are butanediol, neopentyl glycol, hexanediol, propylene glycol, dipropylene glycol, diethylene glycol and/or cyclohexanedimethanol.

The diamines or diols employed in the context of the invention for chain extension are commodity chemicals available from Rheinchemie Rheinau GmbH under the trade name Addolink®.

The proportion of diamine and/or diol is preferably 1 to 20 wt % based on the total mixture.

The term "total mixture" is here to be understood as meaning the sum of the constituents of the mixture for producing the polyurethanes.

Catalysts employed are preferably dibutyltin dilaurates or triethylenediamine in dipropylene glycol.

The catalysts employed in the context of the inventions are commodity chemicals obtainable from Rheinchemie Rheinau GmbH under the trade name Addocat®.

The proportion of catalyst is preferably 0.1 to 5 wt % based on the total mixture.

In a further preferred embodiment of the invention further assistant and added substances, such as preferably demolding agents, flame retardant, UV stabilizers and plasticizers, are added.

In a particularly preferred embodiment of the present invention the bis[3-isopropenyl-α,α-dimethylbenzyl]carbodiimide is employed in an amount of 0.1 to 2 wt %, preferably 0.5 to 1 wt %, based on the total mixture.

In a further preferred embodiment of the present invention the bis[3-isopropenyl-α,α-dimethylbenzyl]carbodiimide is employed in liquid form (liquid phase of matter) preferably at temperatures of 20-50° C., particularly preferably 25-35° C.

Metered addition of the bis[3-isopropenyl-α,α-dimethylbenzyl]carbodiimide according to the invention may be effected either during production of the polyurethane or else may be metered-in to the polyurethane subsequently via mixing apparatuses.

The liquid-state metering in the process according to the invention is effected on batchwise- or continuous-operation, preferably continuous-operation, processing machines, for example single-, twin- or multiscrew extruders, on continuous-operation cokneaders (Buss type) and/or batchwise-operation kneaders, for example of the Banbury type, or on other apparatuses customary in the polymer industry. Said metering may be effected right at the start or in the course of production of the ester-group-containing polymer or right at the start or in the course of processing to afford monofilaments or polymer pellets for example.

The term "liquid-state metered" in the context of the invention is to be understood as meaning that the carbodiimides according to the invention are metered into the continuous- or batchwise-operation processing machines in liquid form (in the liquid phase of matter) by gravimetric or volumetric means. To make this possible, the carbodiimides according to the invention must be liquid and of low viscosity during metering, especially at ambient temperature, as is customary in polymer processing. Liquid-state metering in processing operations uses the continuous-operation metering apparatuses customary in thermoplastics compounding technology. These may be heatable. They are preferably not heatable.

In addition, the present invention further provides for the use of the bis[3-isopropenyl-α,α-dimethylbenzyl]carbodiimide according to the invention for stabilizing polyurethanes.

The present invention further provides for the use of the bis[3-isopropenyl-α,α-dimethylbenzyl]carbodiimide according to the invention for stabilizing polyurethanes by incorporation into the previously produced polyurethane by means of liquid-state metering preferably at temperatures of 20-50° C., particularly preferably 25-35° C.

The polyurethane (PU)-based systems produced by this process feature enhanced stability to hydrolysis.

The purview of the invention encompasses all the hereinabove and hereinbelow recited general or preferred definitions of radicals, indices parameters and elucidations among themselves, i.e. including between the respective ranges and preferences in any desired combination.

The examples which follow serve to elucidate the invention but have no limiting effect.

EXEMPLARY EMBODIMENTS

Example 1

Inventive production of bis[3-isopropenyl-α,α-dimethylbenzyl]carbodiimide based on the isocyanate 3-isopropenyl-α,α-dimethylbenzylisocyanate with cesium carbonate.

Examples 2-6

Production of bis[3-isopropenyl-α,α-dimethylbenzyl]carbodiimide based on the isocyanate 3-isopropenyl-α,α-dimethylbenzylisocyanate with other catalysts as comparative examples.

General Production Procedure for Examples 1-5

30 g of 3-isopropenyl-α,α-dimethylbenzylisocyanate were weighed into a 100 mL of three-necked flask fitted with an internal thermometer, reflux cooler and protective gas inlet and 0.6 g (2 wt %) of the respective catalyst as per table 1 were then added. An argon protective gas stream was passed over the vapor phase in the heating phase. The protective gas was turned off on commencement of $CO_2$ evolution. The mixture was subjected to vigorous stirring for 3.5 h at 195° C. (example 1-5) and the reaction mixture was then filtered once it had cooled to about 100° C. The yield was determined by $^1H$ NMR spectroscopy (400 MHz, $CDCl_3$).

Example 6 corresponds to example 1 from WO-A 2005/111136.

TABLE 1

Yields from the synthesis of the carbodiimide based on the isocyanate 3-isopropenyl-α,α-dimethylbenzylisocyanate (by NMR).

| example | catalyst | T [° C.] | carbodiimide [%] | isocyanate [%] | byproduct [%] |
|---|---|---|---|---|---|
| 1 (inv.) | cesium carbonate | 195 | 93 | 0 | 7 |
| 2 (c) | strontium carbonate | 195 | 0 | 100 | 0 |
| 3 (c) | potassium carbonate | 195 | 0 | 100 | 0 |
| 4 (c) | lithium carbonate | 195 | 0 | 100 | 0 |
| 5 (c) | calcium carbonate | 195 | 0 | 100 | 0 |
| 6 (c) | phospholene oxide | 180 | 37 | not determined | not determined | c = comparative example,
inv. = inventive

As is apparent from table 1 the alkali metals of lithium and potassium and the alkaline earth metal carbonates of calcium and strontium have proven completely inutile in relation to use as catalyst for the carbodiimidization of 3-isopropenyl-α,α-dimethylbenzylisocyanate into bis[3-isopropenyl-α,α-dimethylbenzyl]carbodiimide.

By contrast, cesium carbonate surprisingly exhibits a high catalyst activity for the carbodiimidization and results in yields of above 90% and is thus markedly better than the synthesis via phospholene oxide.

In addition the catalyst according to the invention may be removed simply by filtration while in the case of phospholene oxide as catalyst removal must be effected via a costly and inconvenient distillation under vacuum and the yield is therefore reduced further by this workup.

Hydrolysis Inhibition in TPU

To this end 1.0 wt %/1.5 wt % of the carbodiimide according to the invention (CDI inv) and of the commercially available carbodiimides:

CDI 1=a monomeric aromatic carbodiimide substituted with alkyl groups,

CDI 2=a polymeric aromatic carbodiimide, were incorporated into the commercially available polyester-based thermoplastic polyurethane elastomer (TPU/Desmopan® 2587A) by extrusion using a twin-screw extruder.

Injection molding processes are used to produce test specimens therefrom which were post-heated for 16 h at 80° C. Said specimens were then stored in water at 80° C. and the tensile strength measured at regular intervals.

Table 2 shows the percentage relative tensile strength starting at 100% at day 0.

TABLE 2

| | reference material | extruded 1x | CDI 1 1.5% | CDI 2 1.5% | CDI (inv.) 1.5% | CDI (inv.) 1.0% |
|---|---|---|---|---|---|---|
| day 0 | 100 | 100 | 100 | 100 | 100 | 100 |
| day 5 | 82 | 85 | 83 | 94 | 100 | n.d. |
| day 8 | 63 | 62 | n.d. | n.d. | 91 | n.d. |
| day 14 | 18 | 18 | n.d. | n.d. | 86 | n.d. |
| day 19 | 7 | 7 | 79 | 90 | 83 | n.d. |
| day 26 | 0 | 0 | 76 | 88 | 82 | n.d. |
| day 39 | | | 72 | 88 | 82 | n.d. |
| day 45 | | | 63 | 82 | 76 | 91 |
| day 53 | | | 57 | 88 | 73 | n.d. |
| day 57 | | | 42 | 86 | 76 | n.d. |
| day 63 | | | 21 | 64 | 76 | n.d. |
| day 67 | | | 0 | 13 | 73 | n.d. |
| day 80 | | | | | n.d. | 84 |
| day 94 | | | | | n.d. | 80 |
| day 98 | | | | | 68 | n.d. |
| day 105 | | | | | 71 | n.d. |
| day 112 | | | | | 66 | n.d. |
| day 118 | | | | | n.d. | 81 |
| day 140 | | | | | 61 | n.d. |
| day 143 | | | | | n.d. | 73 |
| day 171 | | | | | n.d. | 76 |
| day 192 | | | | | n.d. | 62 |
| day 196 | | | | | 55, *) | n.d. |
| day 213 | | | | | n.d. | 5 | c = comparative example,
inv. = inventive,
n.d. = not determined,
*) no test specimens remaining The results in table 2 show that the bis[3-isopropenyl-α,α-dimethylbenzyl]carbodiimide produced by the process according to the invention exhibits exceptional hydrolysis inhibition activity in thermoplastic PU (TPU) and is superior to the prior art carbodiimides.

Production and Color Stability of Ester-Based PU Hotmelts

Example 7

A hotmelt based on Dynacoll® 7360, a linear copolyester having primary hydroxyl functions and an average molecular weight of 3500 g/mol which is obtainable from Evonik AG, was produced and additized as follows:
(A) 2 wt % of bis[3-isopropenyl-α,α-dimethylbenzyl]carbodiimide produced by the process according to the invention,
(B) 2 wt % of bis[3-isopropenyl-α,α-dimethylbenzyl]carbodiimide produced by the process from WO-A 2005/111136.

All reported amounts are in wt %.

The hotmelt is produced as follows:

The copolyester Dynacoll®7360 is initially evacuated for 30 minutes at 120° C. 11.67 wt % of diphenylmethanediisocyanate (MDI) based on the total formulation is then added and the mixture is reacted for 60 minutes at 120° C.

The additives were then incorporated into the hot melt and an exposure time to the additives of 1 hour was ensured.

The thus produced and additized hot melts were subjected to thermoageing at 130° C. for 48 hours in a cartridge. The hot-melt was filled into an aluminium cartridge (light- and moisture-tight) and aged in a circulating air oven for 48 hours at 130° C.

After the aging, the color and the foaming behavior of the samples was visually evaluated.

The results of the measurements are compiled in table 3:

TABLE 3

| carbodiimide | color | foaming behavior |
| --- | --- | --- |
| example 7A (inv.) | colorless to very slightly yellow | no foam, very little, if any, bubble formation |
| example 7B (c) | reddish-yellow to reddish-brown | foam formation/severe bubble formation | c = comparative example;
inv. = inventive

SUMMARY

These tests show that use of the carbodiimide according to the invention does not result in any notable disruptive side effects in terms of discoloration and foam formation. In comparison, carbodiimides produced by a synthesis catalyzed with phospholene oxide and still containing traces of organophosphorus compounds exhibit the reported disadvantages of discoloration and foam formation.

What is claimed is:

1. A process for producing bis[3-isopropenyl-α,α-dimethylbenzyl]carbodiimide, the process comprising carbodiimidizing 3-isopropenyl-α,α-dimethylbenzylisocyanate in the presence of 0.1-20 wt % of basic cesium salts at a temperature of 160° C. to 220° C.

2. The process as claimed in claim 1, wherein the basic cesium salts comprise cesium carbonate and/or cesium alkoxide.

3. The process as claimed in claim 1, further comprising filtering off the basic cesium salts following the carbodiimidization.

4. The process as claimed in claim 1, further comprising conducting the carbodiimidization in a solvent.

5. The process as claimed in claim 4, wherein the solvent comprises mono-, di-, tri- or polyalkyl-substituted benzenes and/or dibenzenes where alkyl $C_1$-$C_3$.

6. The process as claimed in claim 5, wherein the alkyl-substituted benzenes are xylenes.

7. The process according to claim 1, wherein the basic cesium salts are present at a concentration of 0.5 to 10 wt %, and the temperature is 180'C to 210° C.

8. The process according to claim 1, wherein the process comprises:
carbodiimidizing 3-isopropenyl-α,α-dimethylbenzylisocyanate in the presence of:
0.1-20 wt % of cesium carbonate and/or cesium alkoxide, and
a solvent, at a temperature of 160° C. to 220° C. for a period of time sufficient for carbodiimidizetion of the 3-isopropenyl-α,α-dimethylbenzylisocyanate; and
filtering off the cesium carbonate and/or cesium alkoxide following the carbodiimidization.

9. The process according to claim 8, wherein:
the carbodiimidizing is in the presence of cesium methoxide and/or cesium ethoxide;
the solvent is at least one xylene;
the basic cesium salts are present at a concentration of 1 to 5 wt %; and
the temperature is 190° C. to 200° C.

10. The process according to claim 1, wherein the basic cesium salts comprise cesium carbonate and/or cesium methoxide and/or cesium ethoxide.

* * * * *